United States Patent [19]
Cantele

[11] Patent Number: 5,277,173
[45] Date of Patent: Jan. 11, 1994

[54] CHEMILUMINISCENT DISPOSABLE LARYNGOSCOPE

[75] Inventor: Fred Cantele, 200 Leslie Dr. #1130, Hallandale, Fla. 33009

[73] Assignee: Fred Cantele, Hallandale, Fla.

[21] Appl. No.: 959,079

[22] Filed: Oct. 9, 1992

[51] Int. Cl.$^5$ .............................................. A61B 1/06
[52] U.S. Cl. ........................................ 126/11; 362/34
[58] Field of Search ............... 128/11, 18, 10, 200.26; 606/3, 14; 273/DIG. 24; 446/219; 362/34; 84, 477 B

[56] References Cited

U.S. PATENT DOCUMENTS

| | | | |
|---|---|---|---|
| 3,576,987 | 5/1971 | Voight et al. | 240/2.25 |
| 3,584,211 | 6/1971 | Rauhut | 362/34 |
| 3,597,362 | 8/1971 | Bollyky et al. | 252/186 |
| 3,598,113 | 8/1971 | Moore et al. | 128/11 |
| 3,766,909 | 10/1973 | Ozbey | 128/11 |
| 4,064,428 | 12/1977 | Van Zandt | 362/34 |
| 4,106,079 | 6/1978 | Drury | 84/477 B X |
| 4,320,745 | 3/1982 | Bhitiyakul et al. | 128/11 |
| 4,570,614 | 2/1986 | Bauman | 128/11 |
| 4,583,527 | 4/1986 | Musicant et al. | 128/11 |
| 4,715,564 | 12/1987 | Kinn et al. | 446/219 X |
| 4,814,- | 3/1989 | Elliott | 362/34 |
| 4,834,077 | 5/1989 | Sun | 128/11 |
| 4,972,300 | 11/1990 | Beisswanger et al. | 362/34 |

FOREIGN PATENT DOCUMENTS

| | | | |
|---|---|---|---|
| 0190014 | 8/1986 | European Pat. Off. | 128/11 |
| 7810989 | 6/1979 | Netherlands | 362/34 |

OTHER PUBLICATIONS

Welch Allyn Disposable Laryngoscope Advertisement, Oct. 1972 (2 sides).

Primary Examiner—Richard J. Apley
Assistant Examiner—Beverly A. Meindl
Attorney, Agent, or Firm—Herbert L. Lerner; Laurence A. Greenberg

[57] ABSTRACT

A chemiluminiscent, disposable laryngoscope is disclosed. The device comprises a handle portion with an end and a blade portion which is integrally formed on the end of the handle portion. The blade points away from the handle portion substantially perpendicularly. Inside the blade there is disposed a container which, upon activation, provides chemiluminiscent light. The blade is, at least in portions thereof, formed of translucent material. The unit is selfcontained, self-lighting and disposable as a whole.

6 Claims, 1 Drawing Sheet

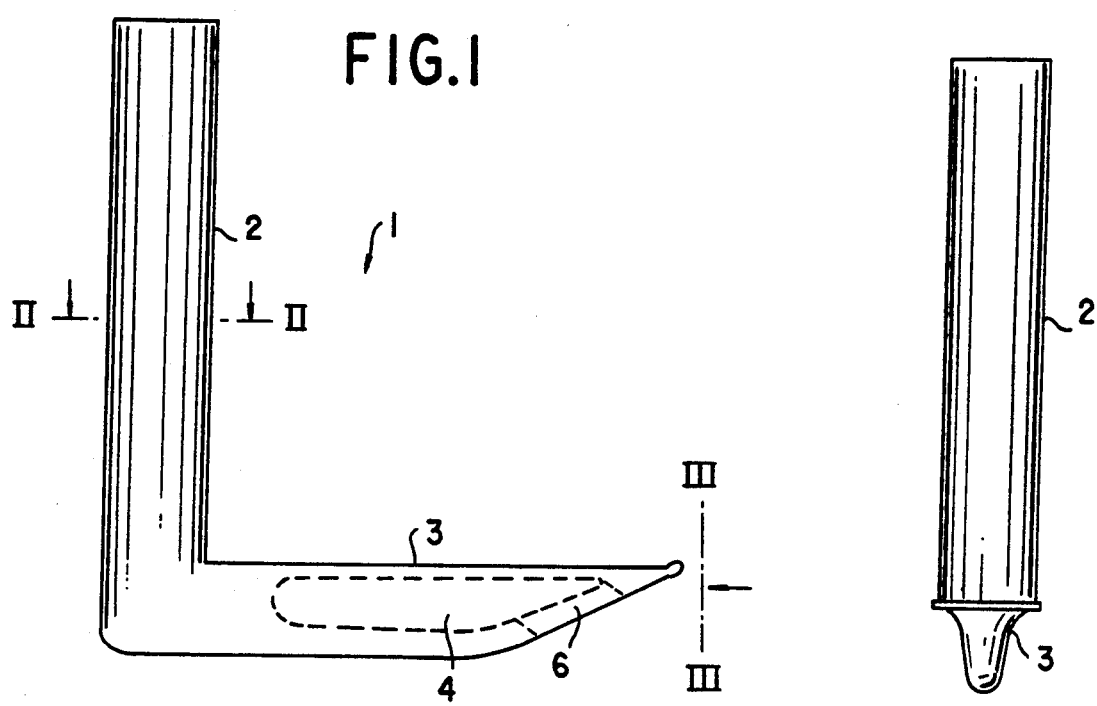
FIG.1
FIG.3
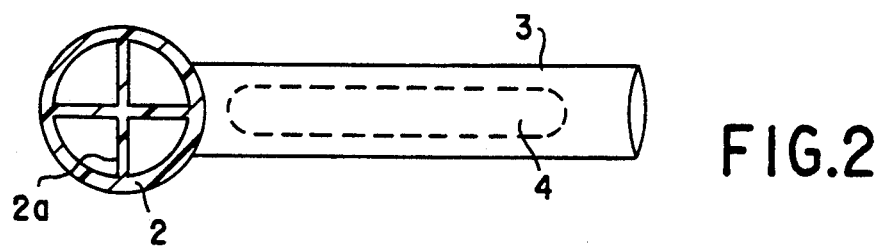
FIG.2
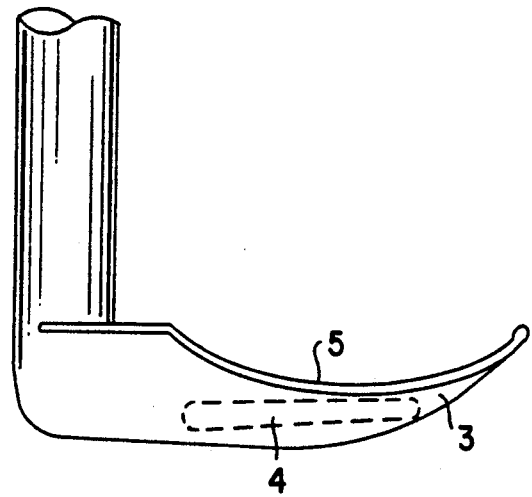
FIG.4

CHEMILUMINISCENT DISPOSABLE LARYNGOSCOPE

BACKGROUND OF THE INVENTION

1. Field of the Invention

The invention relates to a disposable laryngoscope, and more particularly to a self-lighting unit.

Laryngoscopes are medical devices which are used in the examination of the rear oral cavity and the larynx. The device is often used by anaesthesiologists during the insertion of an endotracheal tube in a patient's larynx.

2. Description of the Related Art

Generally, laryngoscopes are used to hold down the tongue, so as to expose and make visible the laryngeal area of the patient. Most modern devices of this kind are comprised of a handle portion and a blade portion affixed thereto. Means for lighting the laryngeal area are incorporated in the device. In many instances the blade is disposable, i.e. the handle is used again after the blade portion has been replaced.

Many such devices have been proposed through the years. U.S. Pat. No. 3,598,113 to Moore provides a handle with a light source incorporated therein. The light energy is transferred through the disposable blade by means of a strand of optical fibers. The light unit, which includes a battery, a lamp and a switch, is retained, while the blade and handle portions are disposed of after use.

U.S. Pat. No. 4,570,614 to Baumann is representative of a type of laryngoscope with a disposable blade portion. The handle portion incorporates a battery pack and a light source. A light conductor guides the light through the blade towards a distal region thereof.

All of the prior art devices have in common that at least one part or another is frequently reused. Especially in light of recent developments and the spreading of AIDS and other transferrable diseases, the prior art devices are seen to be potential transfer carriers.

SUMMARY OF THE INVENTION

It is accordingly an object of the invention to provide a chemiluminiscent disposable laryngoscope, which overcomes the hereinafore-mentioned disadvantages of the heretofore-known devices of this general type and which substantially reduces the potential for the transfer of carrier organisms from one patient to another. Furthermore, it is an object to reduce the cost of the prior art devices, by substantially reducing the component parts of the device.

With the foregoing and other objects in view there is provided, in accordance with the invention, a disposable laryngoscope, comprising a handle portion having an end and a longitudinal axis, a blade portion integrally formed on the end of the handle portion and extending away from the handle portion substantially perpendicularly to the longitudinal axis for insertion into an oral cavity and examining a laryngeal area of a patient, and means disposed in the blade portion for providing chemiluminiscent light.

In accordance with an added feature of the invention, the chemiluminiscent light means are in the form of a chemical lighting device for storing, initiating and displaying chemical light as it is disclosed, for instance, in U.S. Pat. No. 3,576,987. Substances from an outer container are allowed to mix with those from an inner container when the inner container is broken. The ensuing chemical reaction provides the chemical light with which the oral cavity is lighted.

In accordance with an additional feature of the invention, the blade portion has a proximal end at a transition region with the handle portion and a distal end to be inserted in the patient's oral cavity, the blade portion having a curved surface approximately corresponding to the shape of the patient's tongue and having a length to facilitate insertion of the distal end to the patient's epiglottis while the handle portion remains substantially outside the oral cavity.

In accordance with a further feature of the invention, the blade portion has translucent portions formed therein adjacent the chemiluminiscent light means for facilitating lighting of a patient's oral cavity at selected locations when the blade portion is inserted in the oral cavity. By providing "windows" in the blade, the light may be directed at certain locations in the oral cavity.

In accordance with concomitant features of the invention, the blade portion is formed of molded plastic integrally formed on a non-plastic handle portion or, in the alternative, the handle and blade portions are formed as a single, integral unit of molded plastic, and the chemiluminiscent light means are incorporated in the blade portion during the molding of the integral unit.

Other features which are considered as characteristic for the invention are set forth in the appended claims.

The device of the invention is a self-lighting, disposable laryngoscope, and more particularly a self-contained device or unitary construction in which both the handle and the blade are disposable.

In general, the laryngoscope is used for the tracheal intubation of a patient or oral intubation. The claimed laryngoscope is different and unique because it is a one-piece, self-lighting disposable unit. It is to be made of a hard plastic, molded with the blade and handle portions as one piece, an integral unit. The lighting is accomplished by the blade being filled with a non-toxic chemical which produces its own high-intensity light. Such chemiluminiscent chemical substances are commercially available, for instance from American Cyanamid Company.

The laryngoscope is distributed in sealed, antiseptic packages, as usual with medical devices. The laryngoscope is removed from its package, the blade is bent or squeezed by hand until the chemical container inside the blade is broken. Slight shaking mixes the chemical reactants and a high-intensity light is produced. The production of light is almost instantaneous; at this point the instrument is used as a typical laryngoscope. In that the device is to be used only once and then disposed of, it virtually preempts any chance of inter-patient contamination and any spread of infectious disease. Furthermore, since the device is unitarily molded from plastic and a relatively small cartridge of chemiluminiscent substances is incorporated therein during the molding process, the device is quite inexpensive, both in terms of materials and in terms of manufacture.

Although the invention is illustrated and described herein as embodied in a chemiluminiscent disposable laryngoscope, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 1 is a side-elevational view of a first embodiment of the laryngoscope of the invention;

FIG. 2 is a top-plan view of the device of FIG. 1 with a cross-section along the line II—II in FIG. 1 as viewed in the direction of the arrows;

FIG. 3 is a front-elevational view of the device of FIG. 1 as viewed in the direction of the arrow; and FIG. 4 is a side-elevational view of a second embodiment of the device.

DESCRIPTION OF THE PREFERRED EMBODIMENTS

Referring now to the figures of the drawing in detail and first, particularly, to FIG. 1 thereof, there is seen a laryngoscope 1 with a handle 2 and a blade 3. The handle 2 and the blade 3 conventionally enclose an angle of about 90° but other angles are possible as well. Also, the handle 2 may be provided with special gripping surfaces or indentations for the fingers. None of these specific variations are shown, as they are well within the level of ordinary skill in the art.

The handle 2 and the blade 3 form an integral unit made of plastic. Many different plastics may be used. No further information is believed to be required in this context, as those skilled in the plastics art will be able to choose suitable materials in light of the following prescriptions.

The handle 2 must have a certain degree of stiffness. It is thus provided, as seen in the sectional top-plan view of FIG. 2, with ribs 2a which extend longitudinally through the handle 2. Alternatively, the handle may also be solid.

The blade 3 is used to hold the patient's tongue down and, when used by the anesthesiologist, even to slightly pull the patient's jaw forward when inserting the endotrachial tube. Accordingly, it must also exhibit a certain degree of stiffness. In the embodiment shown in FIGS. 1, the blade is relatively stiff and can only be bent slightly in a vertical direction. The sides, however, are soft and flexible so as to allow the blade to be squeezed or bent.

A capsule or cartridge 4 with chemiluminiscent substances is inserted in the blade 3. Such substances are commercially available from American Cyanamid Company, for instance, and they are described in U.S. Pat. No. 3,597,362, which is herewith incorporated by reference. An example of providing a lighting device with a chemiluminiscent cartridge may be found in U.S. Pat. No. 3,576,987, which is herewith incorporated by reference as well.

The cartridge make be "broken" to mix the chemiluminiscent substances and to trigger the necessary reaction by either squeezing the sides of the blade 3 or by bending the same. The blade 3 must thereby be flexibile enough so as to allow the cartridge to "break" and initiate the mixing.

Logically, at least a forward part of the blade 3 portion of the laryngoscope is made of a translucent material. One or more windows 6 may be disposed in the blade portion, so as to allow selective illumination of the oral cavity and laryngeal region. The window 6 is made of a material with a higher degree of translucency than the remaining portions of the blade.

Various shapes are possible for the blade 3. One additional embodiment is shown in FIG. 4. It is understood, however, that the illustrations are but representative and that any of the conventional structures, which are usually formed of metal, can by recast in plastics molds. The blade shown in FIG. 4 has a curved surface 5 which is made to correspond to the patient's upper tongue surface.

By way of example, the handle is cylindrical in shape and approximately six inches long. The handle diameter is about 1¼ inch. Blade length and shapes are variable dependent on usage. In the embodiments shown, the blade is approximately 4¼ inches long, which corresponds to the standard length. The chemiluminiscent cartridge has a diameter of ¼ inch and a length of 1¼ inch for low intensity lighting and a length of about 3 inches for high intensity lighting. The three-inch light stick is available from American Cyanamid Company under model number 95-28113.

I claim:

1. Disposable laryngoscope, comprising a handle portion having an end and a longitudinal axis, a blade portion integrally formed on said end of said handle portion and extending away from said handle portion substantially perpendicularly to said longitudinal axis for insertion into an oral cavity and examining a laryngeal area of a patient, and means disposed in said blade portion for providing chemiluminiscent light, said handle and blade portions being formed as a single integral unit of molded plastic, and said chemiluminiscent light means being incorporated in said blade portion, said blade portion having translucent portions formed therein adjacent said chemi-luminiscent light means for facilitating lighting of a patient's oral cavity at selected locations when said blade portion is inserted in the oral cavity.

2. The disposable laryngoscope according to claim 1, wherein said chemiluminiscent light means are in the form of a chemical lighting device for storing, initiating and displaying chemical light integrally formed into said blade portion.

3. The disposable laryngoscope according to claim 1, wherein said blade portion has a proximal end at a transition region with said end of said handle portion and a distal end to be inserted in the patient's oral cavity, said blade portion having a curved surface approximately corresponding to the shape of the patient's tongue and having a length to facilitate insertion of said distal end to the patient's epiglottis while said handle portion remains substantially outside the oral cavity.

4. The disposable laryngoscope according to claim 1, wherein said blade portion is formed of molded plastic integrally formed on said handle portion.

5. The disposable laryngoscope according to claim 1, wherein said chemiluminiscent light means are incorporated in said blade portion during the molding of said integral unit.

6. The disposable laryngoscope according to claim 1, wherein said blade portion is formed of translucent material.

* * * * *